(12) United States Patent
Ivanov et al.

(10) Patent No.: US 7,166,309 B2
(45) Date of Patent: Jan. 23, 2007

(54) NUTRITIONAL COMPOSITION AND METHOD OF INHIBITING SMOOTH MUSCLE CELL CONTRACTION THEREOF

(75) Inventors: Vadim Ivanov, Castro Valley, CA (US); Svetlana Ivanova, Castro Valley, CA (US); Wahid M. Roomi, Sunnyvale, CA (US); Aleksandra Niedzwiecki, San Jose, CA (US); Matthias Rath, Twenteport Oost 3, NL- 7609 RG Almelo (NL)

(73) Assignee: Matthias Rath, Bocholtz (NL)

( * ) Notice: Subject to any disclaimer, the term of this patent is extended or adjusted under 35 U.S.C. 154(b) by 244 days.

(21) Appl. No.: 10/855,111

(22) Filed: May 26, 2004

(65) Prior Publication Data

US 2005/0019429 A1    Jan. 27, 2005

Related U.S. Application Data

(63) Continuation-in-part of application No. 10/449,828, filed on May 30, 2003.

(51) Int. Cl.
| | |
|---|---|
| *A61K 36/82* | (2006.01) |
| *A61K 33/06* | (2006.01) |
| *A61K 33/32* | (2006.01) |
| *A61K 33/34* | (2006.01) |
| *A61K 33/04* | (2006.01) |
| *A61K 31/375* | (2006.01) |

(52) U.S. Cl. ............... 424/729; 424/729; 424/682; 424/639; 424/630; 514/474

(58) Field of Classification Search .......... None
See application file for complete search history.

(56) References Cited

U.S. PATENT DOCUMENTS 4,840,966 A * 6/1989 Hara et al. ............ 514/456

6,054,128 A * 4/2000 Wakat .................. 424/765

OTHER PUBLICATIONS

Dr. Rath, Natural Health Consultants, Epican Forte, Mar. 1, 1998.*
Dr. Rath, "High Blood Pressure", 2001.*
Tolloczko, et al. Am J Physiol Lung Cell Mol Physiol 278, 2000.*
Marrero, et al. Clin Exp Pharmacol Physiol Jan. 1996.*
Carini, M. et al., "Procyanidins from grape seed protect endothelial cells from peroxynitrite damage and enhance endothelium-dependent relaxation in human artery: new evidences for cardio-protection." *Life Sci*, 73(22):2883-98, Oct. 17, 2003.
Shen, J.Z. et al., "Green Tea catechins evoke a phasic contraction in rat aorta via H2O2-mediated multiple signalling pathways." *Clin Exp Pharmacol Physiol.*, 30(1-2):88-95, Jan-Feb. 2003.
Chen, Z.Y. et al., "Inhibitory effects of purified green tea epicatechins on contraction and proliferation of arterial smooth muscle cells." *Acta Pharmacol Sin.* 21(9): 835-40, Sep. 2000.
Sanae, J.Z. et al., "Effects of catechins on vascular tone in rat thoracic aorta with endothelium." *Life Sci*, 71(21):2553-62, Oct. 11, 2003.
Huang, Y. et al., "Role of endothelium/nitric oxide in vascular response to flavonoids and epicatechin." *Acta Pharmacol Sin.* 21(12): 1119-24, Dec. 2000.
Rudnic, Edward et al., "Oral solid dosage forms," *Remington: The Science and Practice of Pharmacy*, vol. 2, Chapter 92, 1615, 1642-1647, Alfonso R. Gennaro, Ed., 19th Ed., 1995.
International Search Report dated Oct. 21, 2004, Application No. PCT/US04/16902 filed May 26, 2004.

* cited by examiner

*Primary Examiner*—Christopher R. Tate
*Assistant Examiner*—Melenie McCormick
(74) *Attorney, Agent, or Firm*—Ali Kamarei, Esq.

(57) ABSTRACT

The present invention provides for a method of using a nutritional composition in inhibiting smooth muscle cell contraction, and hence lowering hypertension.

10 Claims, 9 Drawing Sheets

NUTRITIONAL COMPOSITION AND METHOD OF INHIBITING SMOOTH MUSCLE CELL CONTRACTION THEREOF

CROSS-REFERENCE TO RELATED APPLICATION

This application is a continuation-in-part of the U.S. Utility application Ser. No. 10/449,828 filed May 30, 2003, the disclosure of which is incorporated by reference in its entirety herein.

FIELD OF THE INVENTION

This invention relates to nutritional composition and method of inhibiting the contraction of smooth muscle cells, and hence may lower blood pressure in hypertensive patients.

BACKGROUND OF THE INVENTION

There are many documented pathophysiological and clinical effects of hypertension. These effects include the short-term effects resulting in poor health and bad work performance and the longer-term effects resulting in myocardial infarction, stroke, cardiac arrest, kidney disease, kidney failure and others. Moreover, the effects of hypertension may be exacerbated in conjunction with other diseases such as diabetes. In recent years it is estimated that more than 50% of deaths relating to cardiovascular disease in the United States alone was related to or resulted from hypertension. Hypertension remains the most common cause of cardiac failure or other disease states requiring some amount of hospitalization.

There has been significant and extensive research for treatment for hypertension. However, present treatments for such disorders are treatments such as administration of angiotensin converting enzyme inhibitors (ACE inhibitors). These treatments have serious shortcomings in long-term effectiveness, most notable the cost associated with these treatments and significant adverse effects.

There are also a vast number of publications with regard to the mechanisms of pathogenesis of hypertension. Extensive production and activity of angiotensin II is well accepted as one of the major sources in the development of hypertension, since its excess causes abnormally strong contraction of arteries, compromises process of arteries relaxation and lead therefore to elevated blood pressure. Thus, a massive effort is being undertaken to develop pharmaceutical compounds capable either to reduce formation of angiotensin II (i.e. ACE inhibitors which block a conversion of angiotensin I to angiotensin II by arterial wall cells) or to block a biological activity of angiotensin II (i.e. agonists of angiotensin receptors). Both classes of compounds are being tested in experimental conditions for their capacity to block angiotensin-dependent contraction of arterial wall either using arteries isolated from laboratory animals or a model of cultured smooth muscle cells embedded in collagen gel. A capacity of a tested compound to block a contractile activity of angiotensin II in such experimental models unequivocally means that this compound will block angiotensin II activity in in vivo conditions and will reduce angiotensin-driven hypertension.

Carini et al. describe procyanidins from grape seeds that enhance relaxation of human artery (*Life Sci.* Oct. 17, 2003; 73(22):2883–98). Shen et al. describe green tea catechins that evoke a phasic contraction in rat aorta, and Chen et al. describe purified green tea epicatechins on contraction. Sanae et al. describe the effects of catechins on vascular tone in rat thoracic aorta with endothelium. Huang et al. describe role of endothelium/nitric oxide in vascular response to flavonoids and epicatechin (*Acta Pharmacol. Sin.* Dec. 21, 2000(12): 1119–24). While these references suggest a possible role of green tea extracts in regulating vascular tone, its direct effect to smooth muscle cells is less clear. Little is know if other ingredients may enhance the effect of green tea extract on smooth muscle cell contraction.

In view of the foregoing, there is a need for a nutritional composition and method to directly inhibit smooth muscle cell contraction and hence treat the underlying hypertension disease. There is a need for a method of using such a nutritional composition to preserve and restore the sensitivity of the arteries to stimuli that would allow for proper contraction and relaxation of smooth muscle cells in the arteries.

SUMMARY OF THE INVENTION

The present invention provides a method of inhibiting smooth muscle cell contraction comprising the step of treating smooth muscle cells with a nutritional composition comprising a green tea extract, ascorbic acid, lysine, proline, arginine, magnesium, N-acetyl cysteine, selenium, copper, and manganese.

Preferably, the green tea extract is at least one compound selected from the group consisting of epicatechin, epicatechin-3-gallate, epigallocatechin and epigallocatechin-3-gallate. More preferably, the green tea extract is epigallocatechin-3-gallate.

Preferably, the ascorbic acid is calcium ascorbate, magnesium ascorbate or ascorbyl palmitate.

Preferably, the step of treating is the step of administering to a human subject. Preferably, the administered nutritional composition comprises 1,000 mg green tea extract, 710 mg ascorbic acid, 1,000 mg lysine, 750 mg proline, 500 mg arginine, 1 mg magnesium, 30 mg N-acetyl cysteine, 30 μg selenium, 2 mg copper, and 1 mg manganese.

Preferably, the nutritional composition further comprises at least one ingredient selected from the group consisting of resveratrol and genistein.

It is an object that the present invention provides a method of administering a nutritional composition that is useful in lowering blood pressure.

It is another object of the present invention to use nutritional compounds from a natural source that is safe.

It is another object of the present invention to provide a method of retarding adverse effects of stimuli, which lead to contraction of smooth muscle cells, which in turn increase blood pressure and results in hypertension.

It is yet another object of the present invention to provide method of administering a nutritional composition wherein the nutritional composition is administered in daily amounts indicated in Table 1.

DETAILED DESCRIPTION OF THE INVENTION

As used herein, the term "EF" refers to a nutritional composition comprising 1,000 mg green tea extract, 710 mg ascorbic acid, 1,000 mg lysine, 750 mg proline, 500 mg arginine, 1 mg magnesium, 30 mg N-acetyl cysteine, 30 μg selenium, 2 mg copper, and 1 mg manganese; lysine includes L-lysine and its derivative, proline includes L-proline and its derivatives, arginine includes L-arginine and its derivatives; SMC refers to smooth muscle cells, EGCG refers to (−)-epigallocatechin-3-gallate, EC refers to epicatechin which refers to (−)-epicatechin, ECG refers to eipcatechin-3-gallate which refers to (−)-epicatechin-3-gallate, EGC refers to epigallocatechin which refers to (−)-epigallocatechin. Plant-derived bioflavonoids include catechins (which include EGCG, EG, ECG and EC) and is implicated to support arterial wall structural integrity and interfere with a variety of pro-atherosclerotic stimuli.

Hypertension as used in this application includes and is defined using the guidelines of the American Heart Associate (AHA) for both hypertensive and pre-hypertensive states. The AHA defines pre-hypertensive state as a systolic blood pressure of between 120 and 139 mmHg and a diastolic blood pressure between 80 and 89 mmHg. The AHA defines hypertensive state as systolic blood pressure of greater 140 mmHg and a diastolic blood pressure greater than 90 mmHg.

The nutritional composition of the present invention includes at least one flavonoid component. The flavonoid component includes green tea extract. The green tea extract is commercially available from U.S. Pharma Lab. (Somerset, N.J.) (product name: GreenHerb—green tea powder extract). The green tea extract contains total polyphenols of about 80% wt. Within the polyphenols, catechins are present in an amount of about 60% wt. Within the catechins, EGCG is present in an amount of about 35% wt. Caffeine is present in the green tea extract (about 1.0% wt).

The nutritional composition of the present invention comprises a green tea extract, ascorbic acid, lysine, proline, arginine, magnesium, N-acetyl cysteine, selenium, copper, and manganese.

Preferably, the nutritional composition of the present invention comprises 500 mg–2,000 mg green tea extract, 400 mg–1,500 mg ascorbic acid, 400 mg–1,500 mg lysine, 500 mg–1,500 mg proline, 200 mg–1,000 mg arginine, 0.5 mg–2 mg magnesium, 10 mg–60 mg N-acetyl cysteine, 10 μg–60 μg selenium, 0.5 mg–5 mg copper, and 0.5 mg–2 mg manganese.

More preferably, the nutritional composition of the present invention comprises 1,000 mg green tea extract, 710 mg ascorbic acid, 1,000 mg lysine, 750 mg proline, 500 mg arginine, 1 mg magnesium, 30 mg N-acetyl cysteine, 30 μg selenium, 2 mg copper, and 1 mg manganese.

Preferably, the nutritional composition further comprises resveratrol or genistein. The preferred doses for resveratrol and genistein are 10–50 μM; and more preferred doses of 10 μM–30 μM.

The nutritional composition of the present invention is intended for administration to a mammal, in particular a human being, in a suitable dosage form as is known in the art. Suitable dosage forms known in the art include parenteral, enteral, and especially oral. Oral solid and liquid dosage forms are particularly preferred. Oral solid dosage forms are well known in the art and include tablets, capsules, and edible food items. Oral solid dosage forms can be made with one or more pharmaceutically acceptable excipients. Pharmaceutical acceptable excipients assist or make possible the formation of a dosage form for a bioactive material and include diluents, binding agents, lubricants, glidants, disintegrants, coloring agents, and flavorants. An excipient is pharmaceutically acceptable if, in addition to performing its desired function, it is non-toxic, well tolerated upon ingestion, and does not interfere with absorption of bioactive ingredients. In another embodiment, these ingredients are prepared in a tablet form. Tablets can be made by well-known compression techniques using wet, dry, or fluidized bed granulation methods. The effective proportions of each specified ingredients (i.e., within the EF composition) are combined with desired amount of a pharmaceutically acceptable excipient (e.g., lactose, starch, dextrin, ethyl cellulose and the like. The ingredients are mixed in a blender. Useful blenders include the twin-shell type, the planetary mixer type, and the high-speed high shear type, all of which are known in the art. Tablets can be either coated or uncoated as is known in the art. Capsules, also known as dry filled capsules, are oral solid dosage forms in which the composition is contained in a swallowable container of suitable size, typical made of gelatin. Hard empty capsules suitable for containing the nutritional composition of the present invention are commercially available. The art of capsule filing is well known in the art (Edward Rudnic and Joseph B. Schwartz, *Oral Solid Dosage Forms*, in Volume II, Remington: The Science and Practice of Pharmacy, Chapter 92, 1615, 1642–1647 (Alfonso R. Gennaro, Ed., 19$^{th}$ Ed., 1995).

Experimental Protocol

The following starting material and equipment were used.
1. Cultured vascular smooth muscle cells (SMC) isolated from human aorta. Cells are used from 4$^{th}$ to 8$^{th}$ passages.
2. Human collagen type I.
3. Angiotensin II.
4. Thrombin.
5. Composition EF (lysine, proline, arginine, vitamin C (as ascorbic acid, calcium ascorbate, magnesium ascorbate, or ascorbyl palmitate), magnesium, N-acetyl cysteine, selenium, copper, and manganese. 6 capsules of composition EF contain 1,000 mg of lysine, 750 mg proline, 500 mg L-Arginine, 710 mg of vitamin C, 50 mg magnesium, 1000 mg standardized green tea extract (80% polyphenols—800 mg (decaffeinated)) 30 mg N-acetyl cysteine, 30 µg selenium, 2 mg copper, 1 mg manganese. (all ingredients commercially available)
6. Epigallocatechin gallate (EGCG)
7. Resveratrol
8. Cell culture medium (DMEM)
9. 24 well plastic cell culture plate pre-incubated with 2 mg/ml bovine serum albumin.
10. Digital camera.
11. Digital image analyzing software (Scion Corporation).

TABLE 1

Composition 1 ("Composition EF")

| Compound | Dosage per day |
| --- | --- |
| L-Lysine | 1,000 mg |
| L-Proline | 750 mg |
| L-Arginine | 500 mg |
| Vitamin C, as ascorbic acid, Calcium Ascorbate, magnesium Ascorbate or Ascorbyl Palmitate | 710 mg |
| Magnesium | 50 mg |
| Standardized Green Tea Extract, 80% polyphenols - 800 mg (decaffeinated) | 1,000 mg |
| N-Acetyl-Cysteine | 200 mg |
| Selenium | 30 mcg |
| Copper | 2 mg |
| Manganese | 1 mg |

Methods:

We tested the ability of green tea extracts (i.e., bioflavonoids) and various ingredients on inhibiting the contractile activity of smooth muscle cells. Cultured human aortic smooth muscle cells (SMC) (commercially available from Clonetics) were used and embedded in a three-dimensional type I collagen (1 mg/mL) matrix. Collagen was obtained from Sigma and the matrix preparation is described below. Gel contraction was stimulated by adding 1 µmolar angiotensin II (Ang II) in serum-free media and the gel area was assessed by digital image analysis after 24 hours.

Culture of Smooth Muscle Cells

Confluent cultures of SMC were removed from culture flask by trypsinization and washed with phosphate-buffered saline (PBS) from serum-containing medium. Cell concentration in suspension was brought to 500,000 cell/mL in serum-free DMEM. Cell suspension was then mixed 1:1 with ice-cold 2 mg/ml collagen type I solution in phosphate buffered solution (PBS). Final concentration of collagen type I was 1 mg/mL, final cell concentration was 250,000/mL.

Collagen-SMC suspensions were distributed by 300 µl to 24 well plates in such a manner to cover the entire bottom surface of the wells. The plates were then incubated for one hour at 37° C. to allow gel to polymerize. 0.5 mL of experimental serum-free medium containing no additions (control), or 1 micromol/L angiotensin II with or without tested compound was added to polymerized gel. Plates were then gently tapped on the side to detach gel from the bottom of plastic well, and plates were then placed to incubator with the controlled atmosphere containing 5% $CO_2$ at 37° C. for incubation. After 24-hour incubation plates were taken from the incubator and plate image with floating gels were taken using digital camera. Gel flat surface area is measured with digital image analyzing software from Scion Corporation. Experiments were performed in triplicates and results are presented as mean+/−SD.

Studies were carried out to observe the effects of various components in composition EF and to determine the synergistic effect of the ingredients in composition EF, if any, in inhibiting smooth muscle cell contraction. These studies may shed light on the treatment and/or prevention of hypertension.

Various ingredients including epigallocatechin gallate (EGCG) was studied. Epigallocatechin gallate and other ingredients were first studied by evaluating the single effect of epigallocatechin gallate and respective ingredients. Synergistic effects between epigallocatechin gallate with other ingredients were then studied.

Results

Both angiotensin II and thrombin (used as agonists) caused contraction of the smooth muscle cells in the SMC gel. These agonists further caused contraction of the entire gel. Addition of angiotensin II or thrombin caused a reduced gel surface area. The differential between the gel surface area at 24 hours after pouring of the SMC gel that does not contain a contracting agent, and the gel surface area at 24 hours after pouring of an SMC gel that does contain a contracting agent is attributed to the effect of the contracting agent.

Using this SMC gel contraction assay, we evaluated various compounds for their ability to inhibit the smooth muscle cell contraction. Among the ingredients in the green tea extracts, epigallocatechin gallate is noted to be the most active inhibitor of gel contraction tested. When added at the concentration of 30 µmole/L. Inhibition of gel contraction by bioflavonoids (including EGCG) did not depend on antioxidant activity, since ascorbic acid did not have any activity in this assay.

EXAMPLE 1

Figure 1:
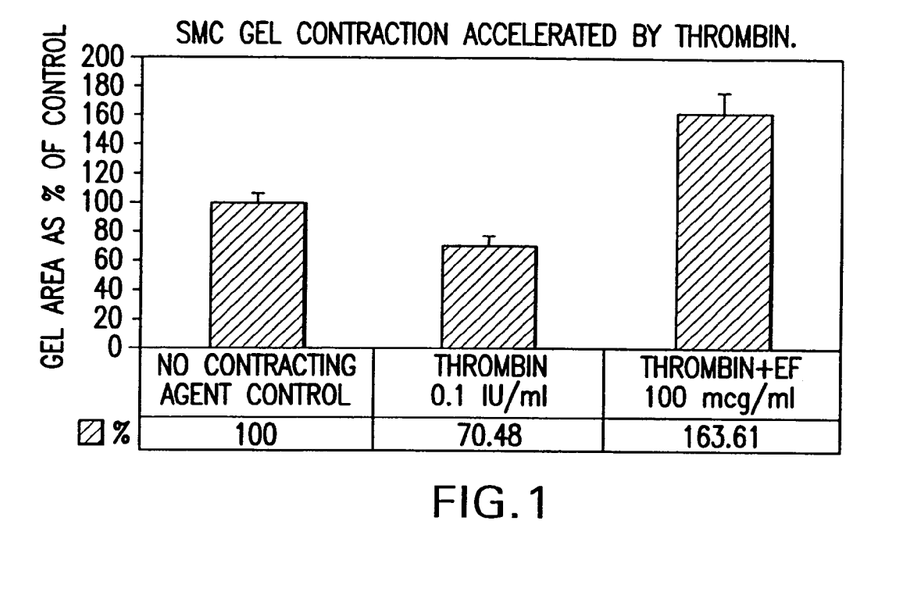
FIG. 1 depicts the effects of 0.1 IU/ml thrombin on smooth muscle cells in SMC gels containing composition 1 ("composition EF") and a control without composition EF. Control SMC gel is without thrombin.

FIG. 1 shows the ability of composition EF in inhibiting smooth muscle cell contraction as induced by thrombin. In this study, a SMC gel without the contracting agent (control) and a gel with the contracting agent (thrombin at 0.1 IU/ml) were compared to a gel with thrombin at 0.1 IU/ml treated with 100 µg/ml of composition EF. Control SMC gels without a contracting agent and treating agent showed some contraction. Thus, smooth muscle cells have a tendency to contract, even without the presence of a contracting agent.

SMC gel with contracting agent thrombin showed greater contraction of the SMC gel. However, when an SMC gel was treated with thrombin at 0.1 IU/ml and composition EF, the SMC gel did not contract as much as an SMC gel with or without the contracting agent by themselves. Thus, composition EF showed significant effect in inhibiting the contraction of the SMC gel and in acting as an anti-hypertensive.

EXAMPLE 2

Figure 2:
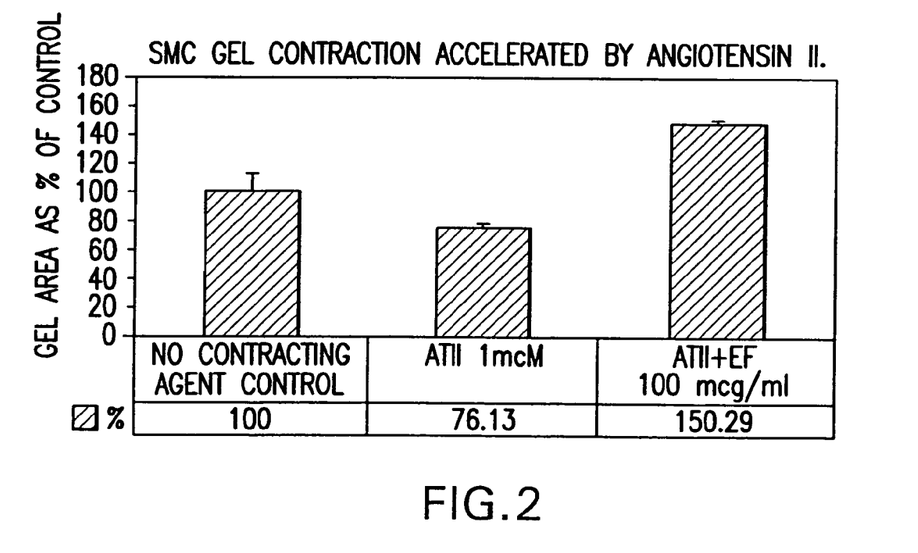
FIG. 2 depicts the effects of 1.0 μM angiotensin II on smooth muscle cells in SMC gels containing composition 1 ("composition EF") and a control without composition EF. Control SMC gel is without angiotensin II.

FIG. 2 shows the ability of composition EF in inhibiting smooth muscle cell contraction as induced by angiotensin II (as an contracting agent). SMC gel without the contracting agent angiotensin II and a gel with the contracting agent angiotensin II at 1.0 µM were compared to a gel with angiotensin II at 1.0 µM treated with 100 µg/ml of composition EF.

SMC gel with contracting agent angiotensin II showed greater contraction of the SMC gel. When a SMC gel was treated with angiotensin II at 1.0 µM and composition EF, the SMC gel did not contract as much as an SMC gel with or without the contracting agent by themselves. Both of these experiments at least tested the premise that composition EF was effective as an anti-hypertensive agent. Accordingly, these data together (FIGS. 1 and 2) clearly show that composition EF is effective in inhibiting the contraction of smooth muscle cells, and thereby may be useful in anti-hypertensive purposes.

EXAMPLE 3

Figure 3:
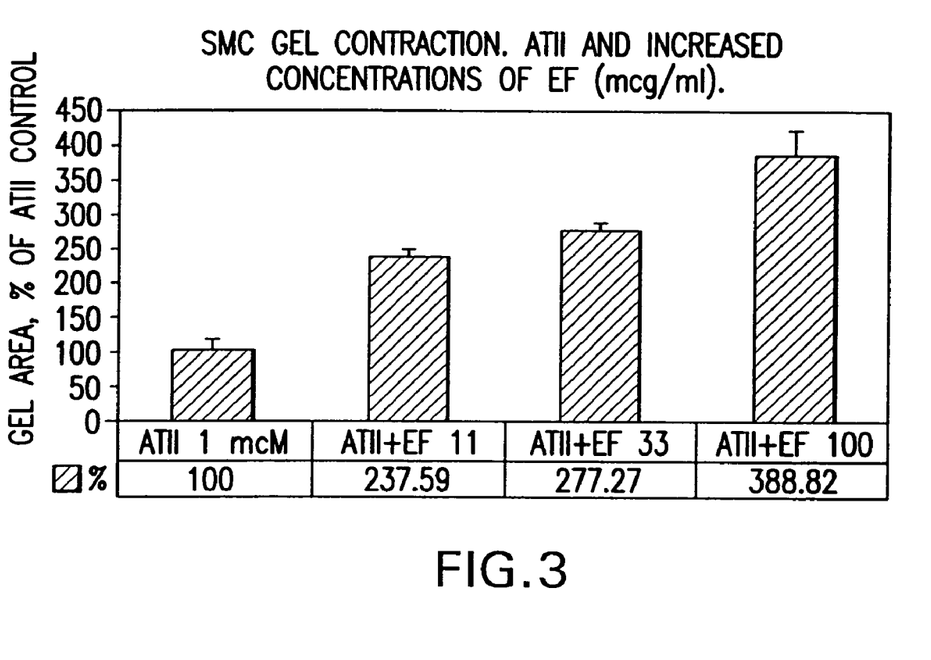
FIG. 3 depicts SMC gel contraction by 1 μM angiotensin II and in the presence of increasing concentrations of composition EF.

FIG. 3 shows a dose-dependent effect of composition EF on inhibiting smooth muscle cell contraction as induced by angiotensin II. SMC gel containing angiotensin II at 1.0 µM was treated with increasing concentrations of composition EF at 11, 33, and 100 µg/ml, and compared to a control of angiotensin II without composition EF. This produced a dose response curve, showing less contraction (greater reduction in SMC gel surface area loss) with increased concentrations of composition EF.

EXAMPLE 4

We next tested respective constituent of the composition EF in inhibiting smooth cell contraction. We also tested if various constituents of composition EF might act in a synergistic manner. To test this, various constituents of composition EF were tested either alone or in combination with other ingredients in their ability to inhibit smooth muscle cell contraction.

Figure 4:
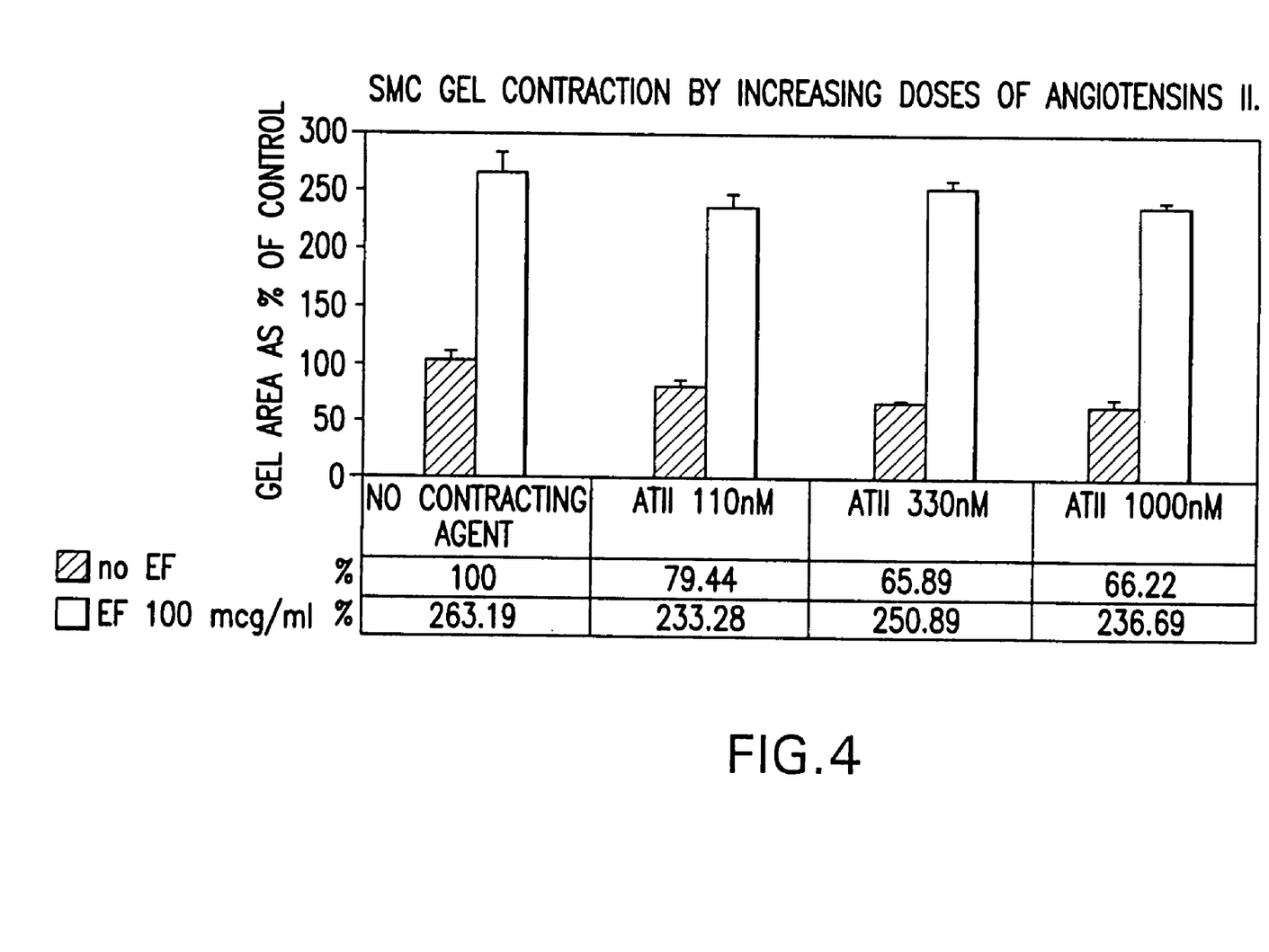
FIG. 4 depicts SMC gel contraction by increasing concentrations of 110 nM, 330 nM, and 1,000 nM angiotensin II and in the presence of 100 μg/ml of composition EF.

FIG. 4 shows the effects of ascorbic acid, EGCG, and ascorbic acid+EGCG on their ability to inhibit smooth muscle cell contraction. SMC gels were induced to contract by angiotensin II (1.0 µM). Control SMC gel contained only angiotensin II. Composition EF at 100 µg/ml greatly inhibit smooth muscle cell contraction. Ascorbic acid at 100 µM alone did not affect angiotensin II induced smooth muscle cell contraction. EGCG at 15 µM alone did not have an appreciable inhibitory effect. The combination of ascorbic acid and EGCG also did not have any appreciable inhibitory effect. These data show that there is a synergistic effect among the various components of composition EF that inhibiting smooth muscle cell contraction. Note that ascorbic acid and EGCG were used at equivalent concentrations found in composition EF.

EXAMPLE 6

Figure 5:
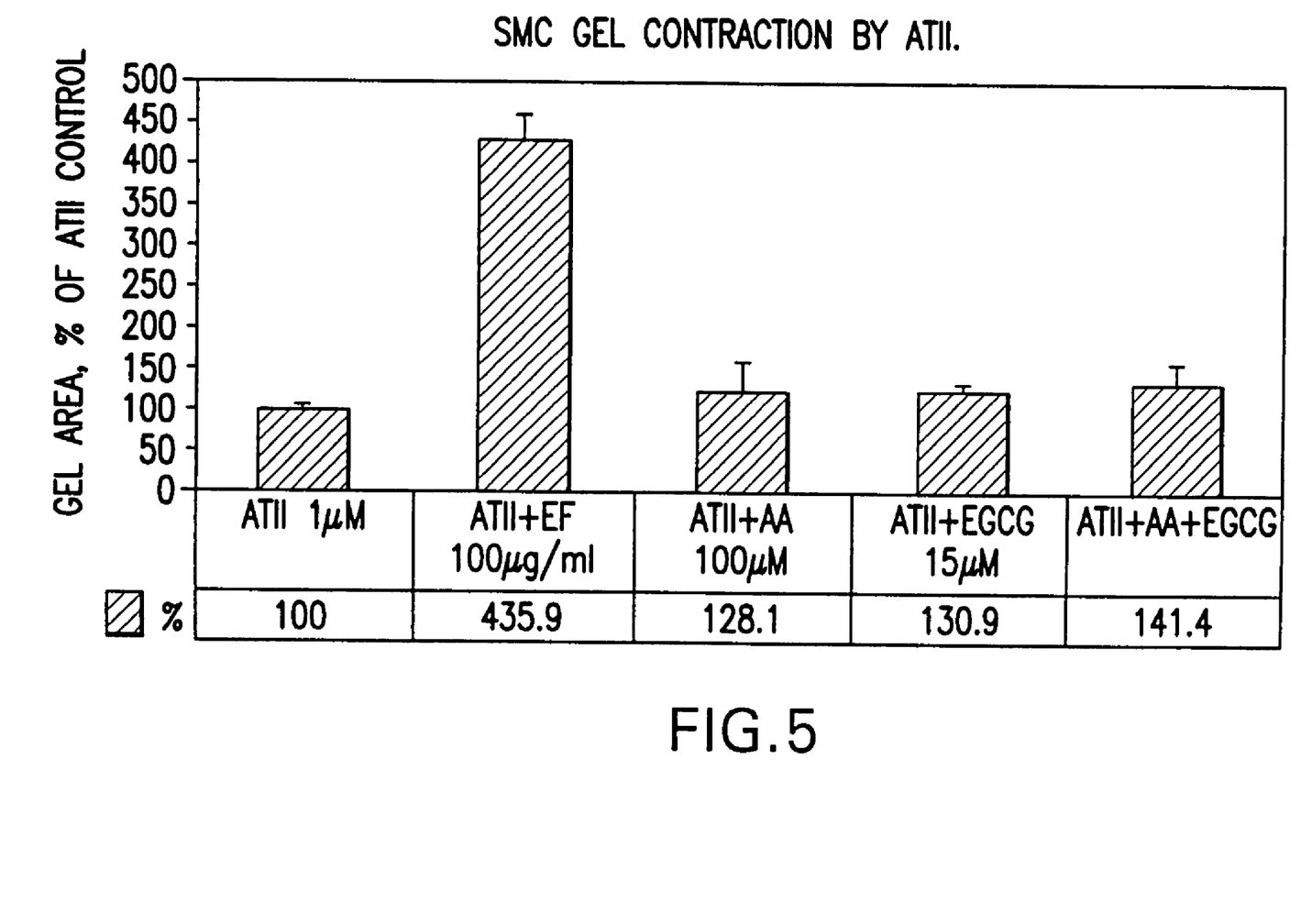
FIG. 5 depicts SMC gel contraction by angiotensin II and in the presence of composition EF, ascorbic Acid, EGCG, and ascorbic Acid-EGCG combination.
Figure 6:
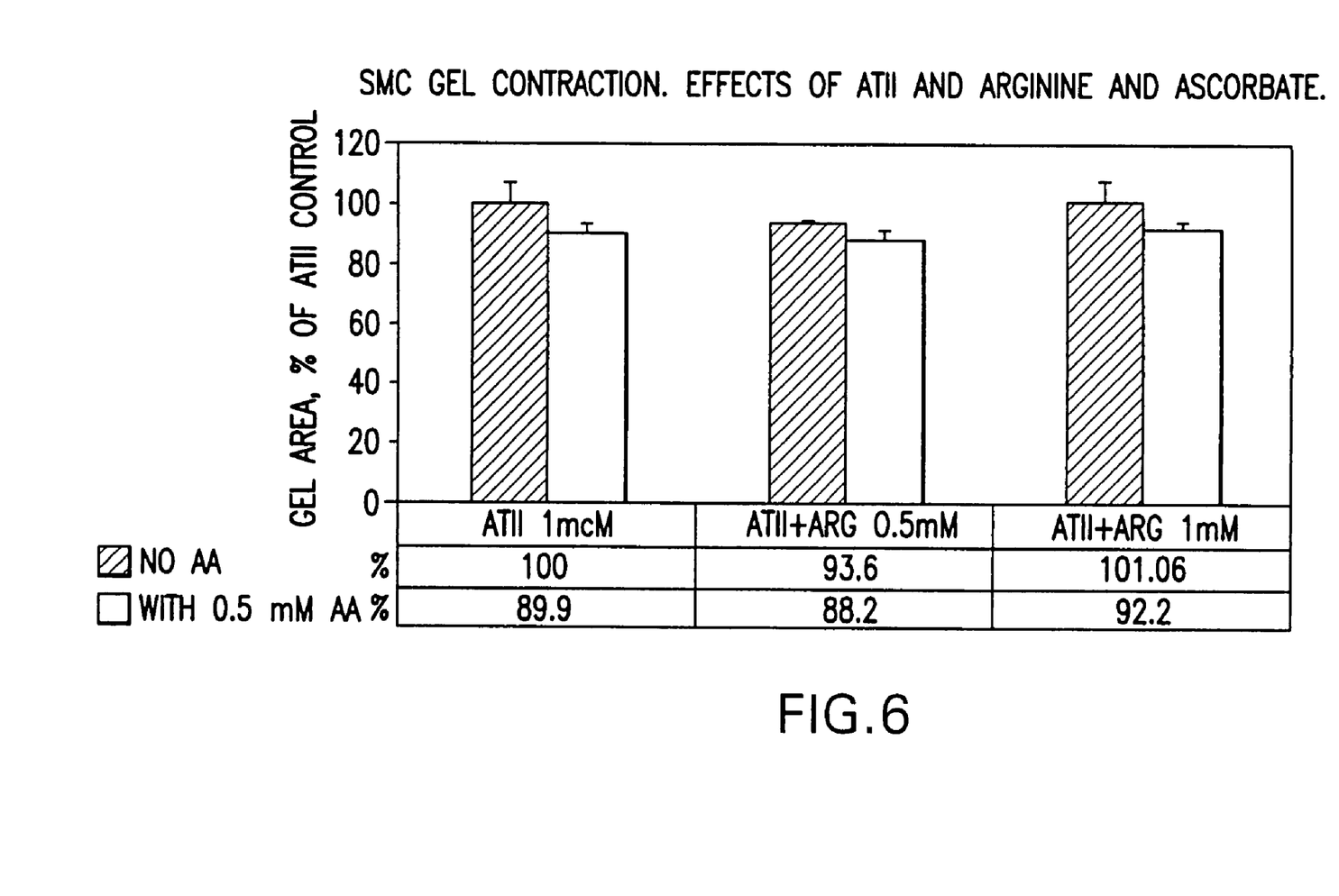
FIG. 6 depicts SMC gel contraction by angiotensin II and in the presence of arginine at various concentrations.

FIG. 5 shows the single effect of arginine on inhibiting smooth muscle cell contraction. Arginine (0.50 mM and 1.0 mM) was applied to SMC gels containing 1.0 µM of angiotensin II and 0.5 mM of ascorbic acid. Equivalent concentrations of arginine were applied to SMC gels containing 1.0 µM of angiotensin II but with no ascorbic acid.

The concentration of arginine in 100 µg/ml of composition EF is 50 µM. Therefore the concentrations of arginine applied singly to the SMC gels were respectively 10 times and 20 times greater than the concentration of arginine in the composition EF. The concentration of ascorbic acid in SMC gels containing ascorbic acid was 0.5 mM, which is 5 times greater than the concentration of ascorbic acid in EF. Despite these higher concentrations, ascorbic Acid and arginine, either alone or in combination did not produce a detectable effect in inhibiting smooth muscle cell contraction.

EXAMPLE 7

Figure 7:
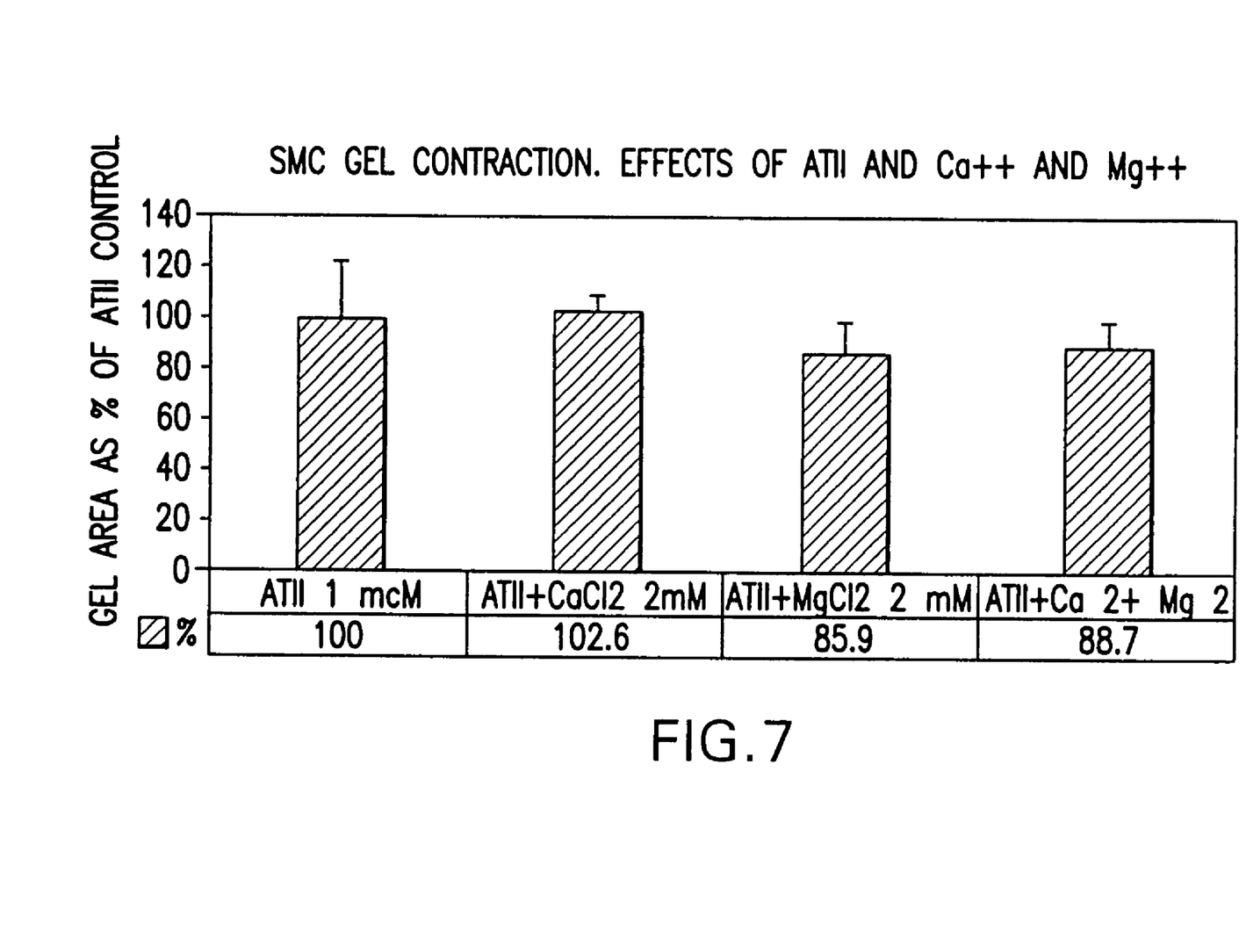
FIG. 7 depicts SMC gel contraction by angiotensin II and in the presence of calcium chloride, magnesium chloride, and calcium chloride-magnesium chloride combination.

FIG. 7 shows the single and combined effect of calcium and magnesium (in the form of calcium chloride and magnesium chloride) on inhibiting smooth muscle cell contraction. The concentration of calcium in 100 µg/ml of composition EF is 12 µM. The concentration of magnesium in composition EF is 50 µM. The concentration of calcium and magnesium used in this study for SMC gel contraction was 2.0 mM. Therefore, the concentrations of calcium and magnesium applied to the SMC gels were respectively approximately 160 times and 40 times greater than the concentration of calcium and magnesium in composition EF. Angiotensin II was added at 1 µM as contracting agent to all SMC gels. Despite these higher concentrations, calcium chloride and magnesium chloride, either alone or in combination, did not produce a detectable inhibition on smooth muscle cell contraction induced by angiotension II.

Figure 8:
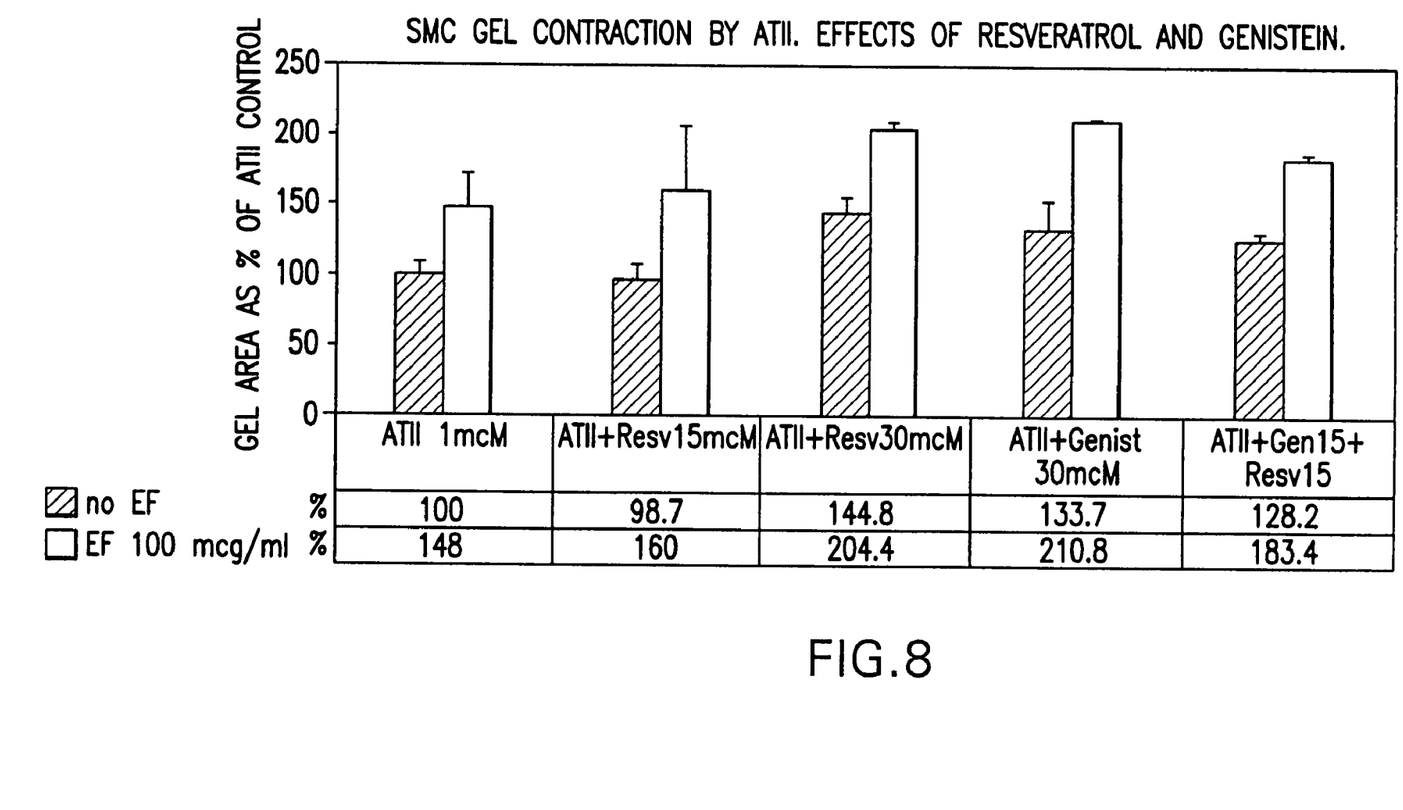
FIG. 8 depicts SMC gel contraction by angiotensin II and the effects of resveratrol and genistein, and in the presence of 100 μg/ml of composition EF.

Although composition EF did not contain any resveratrol or genistein, we tested their combined effect with composition EF. FIG. 8 shows the effects of genistein and resveratrol to either individually or in combination with each other, in inhibiting smooth muscle cell contraction. Resveratrol was applied to SMC gels and compared with SMC gels that did not contain resveratrol. The concentration of resveratrol applied to the SMC gel was 15 µM and 30 µM. In one SMC gel genistein was added at a concentration of 30 µM to test the effect, if any, of genistein by itself. The concentration of resveratrol applied to the SMC gels was 15 µM and 30 µM. Genistein and resveratrol in combination were applied to the SMC gel both at 15 µM. Angiotensin II was added at 1 µM as contracting agent to all SMC gels. Two groups of experiments were carried out, one set of SMC gels without composition EF, and the other set SMC gels containing composition EF at 100 µM.

While resveratrol, genistein, and their combination tended to show some inhibiting effect, this effect was more pronounced when composition EF was present. There was a clear detectable additive anti-hypertensive effect in all SMC gels, whether containing only resveratrol, only ginestein, or both. A dose response curve was evident in the groups containing 15 µM and 30 µM of resveratrol in groups with or without composition EF, however the dose response curve in the resveratrol groups containing Composition EF was more pronounced.

EXAMPLE 8

Figure 9:
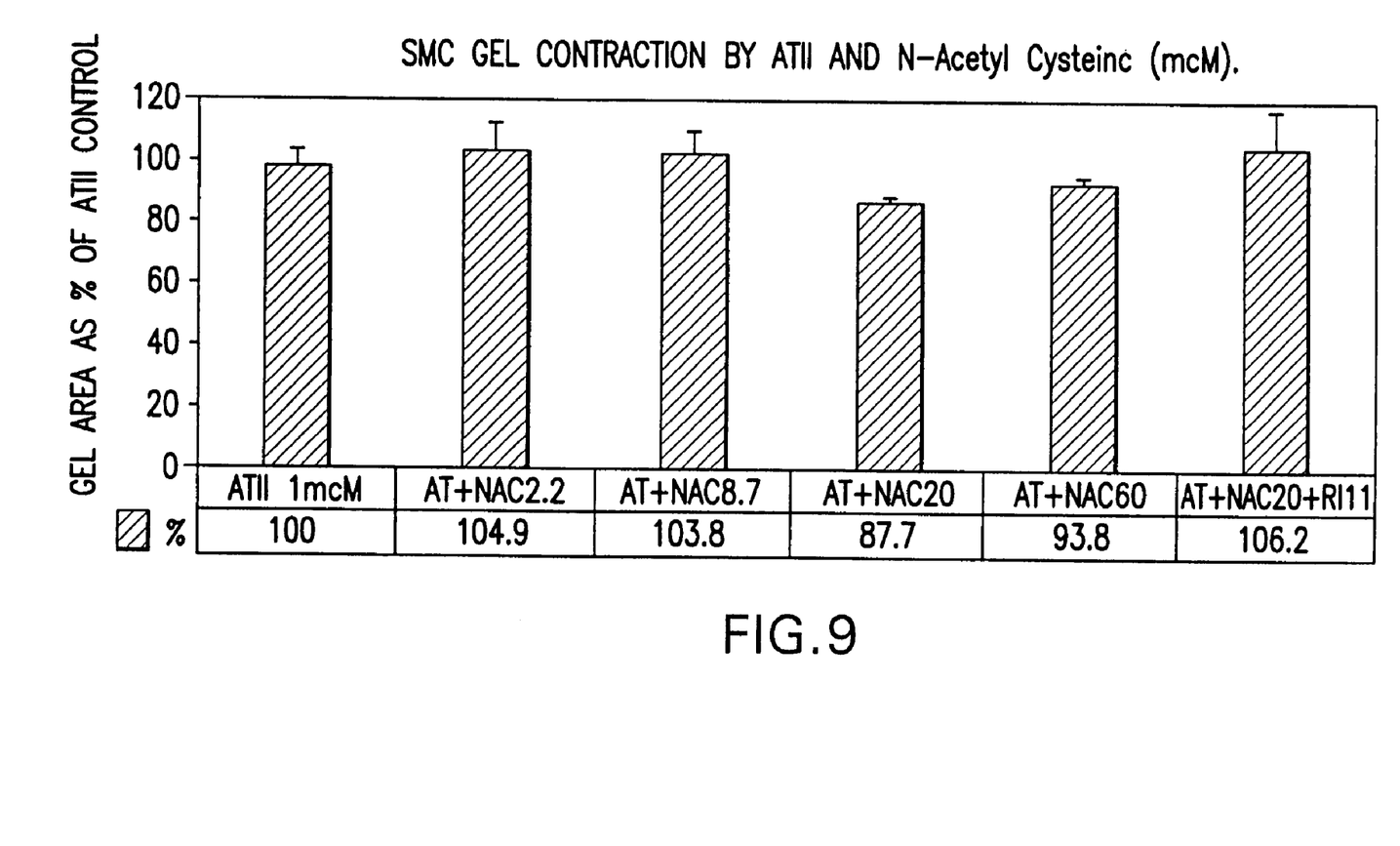
FIG. 9 depicts SMC gel contraction by angiotensin II in presence of various concentrations of N-acetyl cysteine.

FIG. 9 shows the effectiveness of N-acetyl cysteine for inhibiting smooth muscle cell contraction. The concentration of N-acetyl cysteine in 100 µg/ml of composition EF is 20 µM. The concentration of N-acetyl cysteine applied to the SMC gels was 2.2, 6.7, 20 and 60 µM respectively. Angiotensin II was added at 1 µM as contracting agent to all SMC gels. Despite these higher concentrations, N-acetyl cysteine did not produce a detectable anti-contracting effect.

EXAMPLE 9

Figure 10:
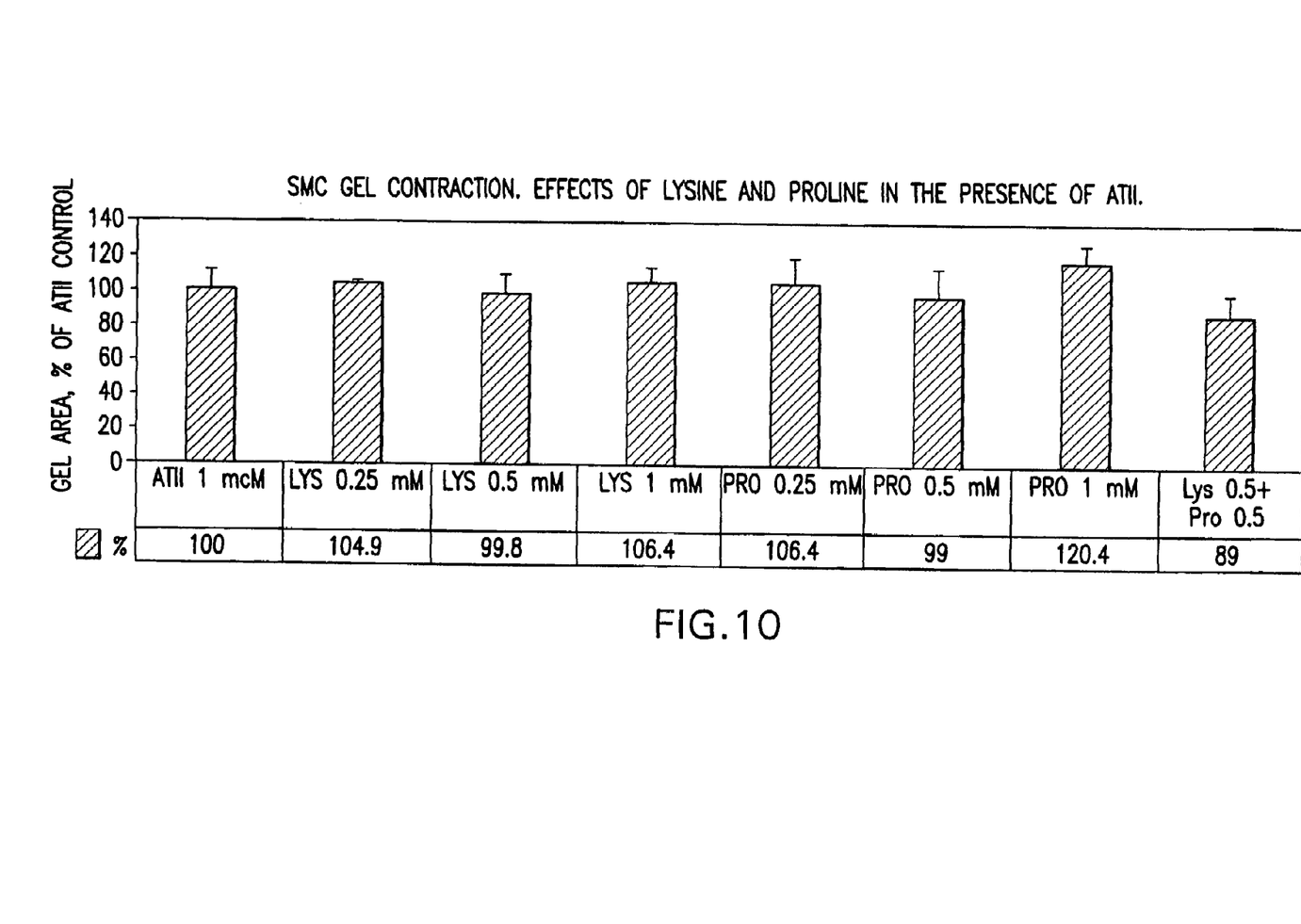
FIG. 10 depicts SMC gel contraction by angiotensin II at 1 μM in the presence of various concentrations of lysine and proline.

FIG. 10 shows the effects of lysine and proline, either individually or in combination with each other, to inhibit smooth muscle cell contraction. The concentration of lysine in 100 µg/ml of composition EF is 110 µM. The concentration of lysine applied to the SMC gels was 0.25, 0.50, and 1 mM. Therefore, the concentrations applied to the SMC gel were respectively approximately 2 times, 4.5 times, and 9 times greater than the concentration of lysine in composition EF. The concentration of proline in 100 μg/ml of composition EF is 100 μM. The concentration of proline applied to the SMC gels was 0.25, 0.50, and 1 mM. Therefore, the concentrations applied to the SMC gel were respectively 2.5 times, 5 times and 10 times greater than the concentration of proline in composition EF. Lysine and proline were added as a combination to an SMC gel at a concentration of 0.50 mM. Angiotensin II was added at 1 μM as contracting agent to all SMC gels. Despite these higher concentrations, proline and lysine, either alone or in combination did not produce a detectable anti-contracting effect.

Together, the results show that a nutritional composition comprising a green tea extract (including ECGC as a bioflavonoid), ascorbic acid, lysine, proline, arginine, magnesium, N-acetyl cysteine, selenium, copper, and manganese, has a synergistic effect in regulation of SMC-mediated contraction. The nutritional composition has a strong potential in counteracting pathophysiological effects of agonists such as thrombin and angiotensin II. While not being bound by a particular mechanism, the synergistic effect seen in composition EF may relate to extracellular matrix integrity.

EXAMPLE 10

We studied the effects of individual catechins on angiotensin II-stimulated contraction of human aortic smooth muscle cells. Catechin (30 μM), epicatechin (30 μM), epicatechin gallate (30 μM), and epigallocatechin gallate (30 μM) were used and angiotensin II was used as stimulant for smooth muscle cell contraction. Gel contraction is represented as percentage of reduction in gel surface area over 24 hour incubation times. Angiotensin II (1 μM) caused 85.26±1.18% (mean±SD) reduction. Angiotensin II (1 μM) plus catechin (30 μM) caused 76.83±1.63% reduction. Angiotensin II (1 μM) plus epicatechin (30 μM) caused 78.59±7.03% reduction. Angiotensin II (1 μM) plus epicatechin gallate (30 μM) caused 65.70±6.56% reduction. Angiotensin II (1 μM) plus epigallocatechin gallate (30 μM) caused 61.23±9.14% reduction.

Accordingly, the present invention provides a possible therapy for a nutritional composition. The components present in the nutritional composition act synergistic in inhibiting smooth muscle cell contraction and hence, reverse and minimize the lack of sensitivity of arteries that lead to hypertension. Furthermore, the present invention provides a potential therapy for a nutritional composition that may retard adverse effects of stimuli, which lead to contraction of smooth muscle cells, which increase blood pressure and results in chronic hypertension. The present invention relates to the selection of compounds and extracts from nature, which are more effective without undue side-effects of pharmaceutical compounds, not to mention its further advantages of economic cost.

It will be understood that there is no intent to limit the present invention to the preferred embodiment disclosed, but rather it is intended to cover all modifications and alternate constructions falling within the spirit and scope of the invention. All publications and other references mentioned herein are incorporated by reference in their entirety.

What is claimed is:

1. A method of inhibiting smooth muscle cell contraction in a human comprising the step of administering a nutritional composition comprising a green tea extract, ascorbic acid, lysine, proline, arginine, magnesium, N-acetyl cysteine, selenium, copper, and manganese to a human in need thereof.

2. The method of claim 1, wherein the green tea extract is at least one compound selected from the group consisting of epicatechin, epicatechin-3-gallate, epigallocatechin and epigallocatechin-3-gallate.

3. The method of claim 2, wherein the green tea extract is epigallocatechin-3-gallate.

4. The method of claim 1, wherein the ascorbic acid is calcium ascorbate, magnesium ascorbate or ascorbyl palmitate.

5. The method of claim 1, wherein the nutritional composition comprises 500 mg–2,000 mg green tea extract, 400 mg–1,500 mg ascorbic acid, 400 mg–1,500 mg lysine, 500 mg–1,500 mg proline, 200 mg–1,000 mg arginine, 0.5 mg–2 mg magnesium, 10 mg–60 mg N-acetyl cysteine, 10 μg–60 μg selenium, 0.5 mg–5 mg copper, and 0.5 mg–2 mg manganese.

6. The method of claim 5, wherein the nutritional composition comprises 1,000 mg green tea extract, 710 mg ascorbic acid, 1,000 mg lysine, 750 mg proline, 500 mg arginine, 1 mg magnesium, 30 mg N-acetyl cysteine, 30 μg selenium, 2 mg copper, and 1 mg manganese.

7. The method of claim 1, wherein the nutritional composition further comprises at least one ingredient selected from the group consisting of resveratrol and genistein.

8. The method of claim 1, wherein the nutritional composition is a dosage form selected from the group consisting of an oral liquid dosage form, an oral solid dosage, tablet and capsule.

9. The method of claim 1, wherein the nutritional composition is useful in lowering blood pressure.

10. The method of claim 1, wherein the nutritional composition is administered in a daily amount as indicated in Table 1.

* * * * *